United States Patent
O'Connell et al.

(10) Patent No.: US 9,855,336 B2
(45) Date of Patent: Jan. 2, 2018

(54) SWINE VIRUS VACCINES THAT ARE LIQUID STABLE

(71) Applicant: Intervet Inc., Madison, NJ (US)

(72) Inventors: Kevin O'Connell, Omaha, NE (US); Zhisong Qiao, Omaha, NE (US); Brad Eddy, Saint Joseph, MO (US); Erin Strait, Spring Hill, KS (US)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 15/119,152

(22) PCT Filed: Feb. 18, 2015

(86) PCT No.: PCT/EP2015/053364
§ 371 (c)(1),
(2) Date: Aug. 16, 2016

(87) PCT Pub. No.: WO2015/124594
PCT Pub. Date: Aug. 27, 2015

(65) Prior Publication Data
US 2017/0014513 A1    Jan. 19, 2017

Related U.S. Application Data

(60) Provisional application No. 61/941,720, filed on Feb. 19, 2014.

(51) Int. Cl.
| | | |
|---|---|---|
| A61K 47/26 | (2006.01) | |
| A61K 39/145 | (2006.01) | |
| A61K 39/225 | (2006.01) | |
| A61K 47/18 | (2017.01) | |
| A61K 39/12 | (2006.01) | |
| A61K 9/00 | (2006.01) | |
| A61K 47/32 | (2006.01) | |
| A61K 39/00 | (2006.01) | |

(52) U.S. Cl.
CPC ............ *A61K 47/26* (2013.01); *A61K 9/0019* (2013.01); *A61K 39/12* (2013.01); *A61K 39/145* (2013.01); *A61K 39/225* (2013.01); *A61K 47/183* (2013.01); *A61K 47/32* (2013.01); *A61K 2039/5254* (2013.01); *A61K 2039/552* (2013.01); *C12N 2760/16034* (2013.01); *C12N 2770/10034* (2013.01); *C12N 2770/20034* (2013.01)

(58) Field of Classification Search
None
See application file for complete search history.

(56) References Cited

U.S. PATENT DOCUMENTS

| | | |
|---|---|---|
| 3,155,589 A | 11/1964 | Slater et al. |
| 3,526,696 A | 9/1970 | Charles |
| 4,337,242 A | 6/1982 | Markus et al. |
| 4,451,569 A | 5/1984 | Kobayashi et al. |
| 5,443,959 A | 8/1995 | Kikuchi et al. |
| 5,565,318 A | 10/1996 | Walker et al. |
| 5,593,824 A | 1/1997 | Tremi et al. |
| 5,763,409 A | 6/1998 | Bayol et al. |
| 5,932,223 A | 8/1999 | Burke et al. |
| 6,039,958 A | 3/2000 | Koyama et al. |
| 6,231,860 B1 | 5/2001 | Fanget et al. |
| 6,331,303 B1 | 12/2001 | Briggs et al. |
| 6,931,888 B2 | 8/2005 | Shekunov et al. |
| 7,073,349 B2 | 7/2006 | Shekunov et al. |
| 7,351,416 B2 | 4/2008 | Briggs et al. |
| 7,959,929 B2 | 6/2011 | Crawford et al. |
| 8,192,747 B2 | 6/2012 | Vande Velde |
| 8,980,610 B2 | 3/2015 | Selvitelli et al. |
| 9,314,519 B2 | 4/2016 | Qiao et al. |
| 9,393,298 B2 | 7/2016 | Buchanan et al. |
| 2004/0038878 A1 | 2/2004 | Tanikawa et al. |
| 2004/0154317 A1 | 8/2004 | Shekunov et al. |
| 2005/0178020 A1 | 8/2005 | Shekunov et al. |
| 2007/0148765 A1 | 6/2007 | Evans et al. |
| 2007/0161085 A1 | 7/2007 | Trager et al. |
| 2007/0190163 A1 | 8/2007 | Malaknov et al. |
| 2007/0259348 A1 | 11/2007 | Phadke et al. |
| 2008/0166784 A1* | 7/2008 | Chen .................. A61K 9/0019 435/235.1 |
| 2008/0248551 A1 | 10/2008 | Stinchcomb et al. |
| 2009/0010955 A1 | 1/2009 | Kapil et al. |
| 2009/0274734 A1 | 11/2009 | Daamen et al. |
| 2010/0015180 A1 | 1/2010 | Francon et al. |
| 2010/0124557 A1 | 5/2010 | Oberreither et al. |
| 2010/0196420 A1 | 8/2010 | Kapil |
| 2010/0297231 A1 | 11/2010 | Vehring et al. |
| 2011/0081380 A1 | 4/2011 | Francon et al. |

(Continued)

FOREIGN PATENT DOCUMENTS

| | | |
|---|---|---|
| EP | 0028563 A1 | 5/1981 |
| EP | 0650734 | 10/1993 |

(Continued)

OTHER PUBLICATIONS

Burke et al. (Critical Reviews in Therapeutic Drug Carrier Systems. 1999; 16 (1): 1-83).*
Medi (European Pharmaceutical Review. 2014; 19 (1): 16-20).*
Auser et al. (Human Vaccines. 2007; 3 (3): 68-77).*
Morefield (The AAPS Journal. Jun. 2011; 13 (2): 191-200).*
Ruiz-Fons et al. (The Veterinary Journal. 2008; 176: 158-169).*
Hanley. (Evolution: Education and Outreach. 2011; 4(4): 635-643).*
Saif ("Bovine respiratory coronavirus." Veterinary Clinics of North America: Food Animal Practice 26.2 (2010): 349-364).*
Ellingson, et al., Vaccine efficacy of porcine reproductive and respiratory Syndrome Virus Chimeras, Vaccine, 2010, pp. 2679-2686, 28.
International Search report for PCT/EP2015/053364 dated Aug. 12, 2015, 16 pages.

(Continued)

*Primary Examiner* — Shanon A Foley

(57) ABSTRACT

The present invention is drawn to liquid stable swine vaccines that comprise a live porcine virus. The invention is also drawn to the manufacture of such vaccines and methods of vaccinating animal subjects with these vaccines.

23 Claims, No Drawings

(56) References Cited

U.S. PATENT DOCUMENTS

| | | |
|---|---|---|
| 2012/0213810 A1 | 8/2012 | Burgard et al. |
| 2014/0056942 A1 | 2/2014 | Qiao et al. |
| 2016/0346381 A1 | 12/2016 | Qiao et al. |
| 2017/0014513 A1* | 1/2017 | O'Connell ............ A61K 39/12 |

FOREIGN PATENT DOCUMENTS

| | | |
|---|---|---|
| EP | 1123710 A1 | 8/2001 |
| GB | 1575155 | 9/1980 |
| JP | 61053227 | 3/1986 |
| WO | 8906973 A1 | 8/1989 |
| WO | 03087327 A2 | 10/2003 |
| WO | 2004017990 A1 | 3/2004 |
| WO | 2007035455 A2 | 3/2007 |
| WO | 2007056847 A1 | 5/2007 |
| WO | 2008107908 A1 | 9/2008 |
| WO | 2008143782 A1 | 11/2008 |
| WO | 2009109550 | 9/2009 |
| WO | 2010125084 A1 | 11/2010 |
| WO | 2010125087 A1 | 11/2010 |
| WO | 2009092703 A1 | 6/2011 |
| WO | 2011072218 | 6/2011 |
| WO | 2014009328 A1 | 1/2014 |
| WO | 2014029702 A1 | 2/2014 |
| WO | 2014140239 A1 | 9/2014 |
| WO | 2015044337 A2 | 4/2015 |
| WO | 2015121463 A2 | 8/2015 |
| WO | 2015124594 A1 | 8/2015 |

OTHER PUBLICATIONS

Morefield, Gary, A Rational, Systematic Approach for the Development of Vaccine Formulations, The AAPS Journal, 2011, pp. 191-200, 13-2.
Papatsiros, Porcine Respiratory and Reproduction Syndrome Virus Vaccinology: A Review for Commercial Vaccines, American Journal of Animal and Veterinary Sciens, 2012, pp. 149-158, 7-4.
Schlehuber, et al., Toward Ambient Temperature-stable vaccines: The identification of thermally stabilizing liquid formulations for measles virus using an innovative high-throughput infectivity assay, Vaccine, 2011, pp. 5031-5039, 29.
Anonymous, "Nobivac DHPPI"—XP002714517,Retrieved from the Internet: URL:http://www.msd-animal-health.co.nz/binaries/ Nobivac DHPPi website label Feb. 12 t cm51-37104.pdf - - - - [retrieved on Oct. 10, 2013] the whole document.
Arakawa, et al., Biotechnology applications of amino acids in protein purification and formulations, Amino Acids, 2007, 587-605, 33.
Ausar, et al., Analysis of the Thermal and pH Stability of Human Respiratory Syncytial Virus, Molecular Pharmaceutics, 2005, 491-499, 2-6.
Brandau, et al., Thermal Stability of Vaccines, Journal of Pharmaceutical Sciences, 2003, 218-231, 92-2.
Cavanagh, et al., Coronavirus avian infectious bronchitis virus, Veterinary Research, 2007, pp. 281-297.
Chen, et al., Opportunities and challenges of developing thermostable vaccines, Expert Reviews, 2009, 547-557, 8-5.
Chokephaibulkit et al., Challenges for the formulation of a universal vaccine against dengue, Experimental Biology and Medicine, 2013, pp. 566-578, 238.
Crawford, et al., Transmission of Equine Influenca Virus to Dogs, Science, 2005, 482-485, 310, US.
Derwent; English Abstract of JP61053227; Title: Mixed live vaccine for Japanese encephalitis and swine parvovirus infection; Sasaki; Mar. 17, 1986.
Intervet UK Ltd., The UK's Favourite Small Animal Vaccines; the Nobivac Range, Nobivac, The Future of Vaccination, 2006, XP002714516; 1-48, 1.
Kamerzell, et al., Protein-excipient interactions: Mechanisms and biophysical characterization applied to protein formulation development, Advanced Drug Delivery Reviews, 2011, 1118-1159, 63.
Lee, et al., Dog-bites and local infection with Pasteurella septica, British Medical Journal, 1960, pp. 169-171, 1.5167.
Mochizuki, Masami, Growth characteristics of canine pathogenic viruses in MDCK cells cultured in RPMI 1640 medium without animal protein, Vaccine, 2006, pp. 1744-1748, 24.
Patel, et al., Stability Consideration for Biopharmaceuticals, Part 1, BioProcess Technical, 2011, 1-10.
Schering-Plough Animal Health Ltd., Nobivac DHPPi; Combined Live Attenuated Freeze-Dried Canine Distemper Virus, Adenovirus Type 2, Parvovirus and Parainfluenza Virus Vaccine, Restricted Veterinary Medicine, 2013, XP002714517; 1-2, 1.
Taguchi, et al., Antibody titers for canine parvovirus type-2, canine distemper virus, and canine adenovirus type-1 in adult household dogs, Canine Veterinary Journal, 2011, 983-986, 52.
Tompkins, et al., Recombinant parainfluenza virus 5 (PIV5) expressing the influenza A virus, Virology, 2007, pp. 139-150, 16(1).

* cited by examiner

SWINE VIRUS VACCINES THAT ARE LIQUID STABLE

CROSS-REFERENCE TO RELATED APPLICATIONS

This application is a national stage entry under 35 U.S.C. §371 of PCT/EP2015/053364 filed on Feb. 18, 2015, which claims priority to U.S. Provisional Application 61/941,720 filed on Feb. 19, 2014. The content of PCT/EP2015/053364 is hereby incorporated by reference in its entirety.

CROSS-REFERENCE TO RELATED APPLICATIONS

This application claims priority under 35 U.S.C. §119(e) of provisional application U.S. Ser. No. 61/941,720 filed Feb. 19, 2014, the contents of which are hereby incorporated by reference in their entireties.

FIELD OF THE INVENTION

The present invention pertains to liquid stable porcine vaccines that comprise a live porcine virus. The invention also pertains to the manufacture of such vaccines and methods of vaccinating animal subjects.

BACKGROUND

There are a significant number of viruses that can infect swine. Such viruses include porcine reproductive and respiratory syndrome virus (PRRS), transmissible gastroenteritis virus (TGE), porcine pseudorabies virus (PPRV), porcine parvovirus (PPV), swine influenza virus (SIV), porcine rotavirus (PRV) and porcine epidemic diarrhea virus (PED). In addition, there are a number of bacteria that can infect swine too, including *Pasteurella multocida* of multiple serotypes, *Salmonella* ssp., *Escherichia coli* of multiple pillus types, *Haemophilus parasuis*, *Lawsonia intracellularis*, *Mycoplasma* ssp., *Bordetella bronchiseptica*, *Erysipelas* ssp., *Campylobacter* ssp., *Actinobacillus pleuropneumoniae*, *Clostridium perfringens* and *Clostridium difficile*.

It is now widely accepted that the best way of preventing disease due to bacterial or viral infections in swine is to vaccinate them against these organisms. Moreover, multivalent live attenuated viral or bacterial vaccines can be safely administered that limit the number of vaccine injections required. Accordingly, there are many commercially available multivalent live virus vaccines that protect against multiple pathogens. However, heretofore, live attenuated swine viruses have been unstable when stored in liquid solutions. Therefore, most live attenuated swine virus vaccines are lyophilized, i.e., freeze-dried or frozen, prior to their long-term storage. The live attenuated porcine virus is commonly mixed as a suspension in water with a protective agent, frozen, and then dehydrated by sublimation and secondary drying during the lyophilization process. The low temperatures of freezing and drying by sublimation, together with the low surface to volume ratios involved, can require long drying periods and thereby, significantly increase manufacturing time and costs.

In addition, there are inherent inconsistencies in large commercial drying processes due to: the inability to adjust the shelf temperature across the entire product load, variable freezing rates across the dryer, edge effects, and radiant energy effects. Increasing the drying temperature to reduce drying times is often not an option since the drying temperature has to remain significantly below the glass-transition temperature of the protective protein matrix. Moreover, the long inconsistent drying times and/or high drying temperatures often lead to structural damage to the live attenuated viruses, along with a significant loss of their biologic activity.

Consequently, in order to account for the inherent loss in efficacy, lyophilized swine vaccines that comprise live attenuated viruses are manufactured with augmented titers. However, such increased titers can lead to significant adverse events should the lyophilization process actually lead to less loss of activity than anticipated. This is particularly problematic for the swine farmer because, at minimum, such an adverse event often leads to lower daily weight gain for the pigs, which translates to lower profits at sale. Therefore, great care is required to formulate a vaccine to contain a virus titer that is not only safely below the amount that leads to adverse events, but that also maintains sufficient efficacy in view of the virus titer loss due to lyophilization and subsequent storage.

Furthermore, there is a limitation to the size of a lyophilization vials and/or number of doses contained within such vials due to relatively small standard stopper sizes for the tops of these vials. Therefore, large volumes of liquid become difficult to sublimate through the relatively small openings. Therefore, there is a need for new live attenuated porcine virus vaccines that can reliably retain their virus titers at a safe and efficacious level.

Additionally, it is not economical to produce swine vaccines in single dose vials. However, vials of lyophilized vaccines must be used in their entirety after rehydration of the freeze dried cake. This makes it difficult for the growing number of small swine farmers who cannot take advantage of the economics of a larger package presentation with a greater number of doses to vaccinate only a few pigs. There is therefore a need for swine vaccines where a single vial can be used over multiple days, weeks or even months, thus reducing the cost and encouraging vaccination of smaller herds.

Finally, due to the nature of lyovials, there is a limitation to the size of the vial and the amount of the liquid that can be lyophilized within. This means that large production facilities must rehydrate multiple bottles in order to vaccinate hundreds, if not thousands of pigs at a time. Once rehydrated in the glass vials, in accordance to the regulations for live vaccine organisms, the glass vials themselves become hazardous waste and must be sterilized or disinfected, buried or burned. Sterilization becomes difficult on the swine farm and often these vials are just discarded into the trash. On the other hand, the use of a liquid stable vaccine would not need to be restricted by being placed into small glass containers, but rather the vaccine could be stored in plastic bags that could have a large range in sizes. Moreover, following the administration of the vaccine to the swine, the plastic bags can easily be destroyed by burning in a small contained fire.

The citation of any reference herein should not be construed as an admission that such reference is available as "prior art" to the instant application.

SUMMARY OF THE INVENTION

In order to overcome the deficiencies of current vaccines, the present invention provides novel liquid stable, live, porcine virus vaccines, as well as their corresponding immunogenic compositions. The liquid stable, live, porcine virus vaccines of the present invention can remain efficacious for extended periods such as 6, 7, 9 months or longer (e.g., about 1 to up to 3 years). The present invention also provides methods of administering such vaccines to a pig. The present invention further provides methods of preventing a disease in an animal, e.g., a pig, through administering a vaccine of the present invention.

Accordingly, the present invention provides liquid stable vaccines, including multivalent vaccines that comprise a live virus. In certain embodiments the live virus is an attenuated virus. In other embodiments the live virus is a recombinant virus. In particular embodiments the live virus is both attenuated and recombinant. Recombinant viruses of the present invention can also encode a heterogeneous protein. In particular embodiments of this type, the heterogeneous protein is a virus, parasite or bacterial antigen.

In particular embodiments, the vaccine comprises a sugar additive that is a sugar alcohol and/or an amino acid. In certain embodiments the vaccine comprises 5 to 40% (w/v) of a sugar alcohol. In particular embodiments, the vaccine comprises 10 to 30% (w/v) of a sugar alcohol. In particular embodiments, the vaccine comprises 15 to 25% (w/v) of a sugar alcohol. In related embodiments the vaccine comprises 10 to 20% (w/v) of a sugar alcohol. In other embodiments, the vaccine comprises 20 to 25% (w/v) of a sugar alcohol. In still other embodiments, the vaccine comprises 25 to 40% (w/v) of a sugar alcohol.

In more particular embodiments, the vaccine comprises 12 to 18% (w/v) of a sugar alcohol. In even more particular embodiments, the vaccine comprises about 15% (w/v) of a sugar alcohol. In related embodiments, the vaccine comprises about 23% (w/v) of a sugar alcohol. In certain embodiments, the liquid stable virus vaccines of the present invention comprise two or more sugar alcohols, with the total amount of the sugar alcohol in the liquid stable vaccines being 5-40% (w/v). In other such embodiments, the liquid stable virus vaccines of the present invention comprise two or more sugar alcohols, with the total amount of the sugar alcohol in the liquid stable vaccines being 25-40% (w/v).

In particular embodiments of the liquid stable virus vaccines of the present invention the sugar alcohol is sorbitol. In an alternative embodiment of this type, the sugar additive is mannitol. In related embodiments, the liquid stable vaccines further comprise a sugar additive that is a non-sugar alcohol, wherein the total amount of the sugar alcohol and the non-sugar alcohol in the liquid stable vaccine is 15-40% (w/v). In other embodiments the liquid stable vaccines further comprise a sugar additive that is a non-sugar alcohol in which the total amount of the sugar alcohol and the non-sugar alcohol in the liquid stable vaccine is 25-40% (w/v). In particular embodiments, the non-sugar alcohol, sugar additive is trehalose. In still other embodiments, the non-sugar alcohol, sugar additive is dextrose. In yet other embodiments, the non-sugar alcohol, sugar additive is sucrose. In particular embodiments of this type, the sugar additive is a combination of sucrose (non-sugar alcohol) and sorbitol (sugar alcohol). In more particular embodiments of this type, the sugar additive is a combination of 10-25% sorbitol and 5-20% sucrose. In other embodiments of this type, the sugar additive is a combination of 15-30% sorbitol and 10-25% sucrose. In still more particular embodiments of this type, the sugar additive is a combination of 15% sorbitol and 10% sucrose. In particular embodiments the non-sugar alcohol, sugar additive is actually a combination of two or more non-sugar alcohol, sugar additives.

The liquid stable vaccines of the present invention can range in pH from pH 6.0 to pH 8.0. In certain embodiments the pH range is from pH 6.5 to pH 7.8. In particular embodiments the pH range is from pH 6.8 to pH 7.5. In other particular embodiments the pH range is from pH 6.6 to pH 7.4. In more particular embodiments the pH range is from pH 7.0 to pH 7.4. In an even more particular embodiment the pH is 7.2.

The liquid stable vaccines of the present invention can comprise a buffer. In a particular embodiment of this type, the buffer comprises 2.5 to 50 mM phosphate, e.g., sodium phosphate (NaPHOS) or potassium phosphate (KPHOS). In a related embodiment, the buffer comprises 5 to 25 mM phosphate. In particular embodiments, the buffer comprises 10 to 20 mM phosphate.

In yet other embodiments the buffer (i.e., buffer solution) can further comprise 0.15 to 0.75 M arginine. In particular embodiments the buffer comprises 2.5 to 50 mM phosphate and 0.15 to 0.75 M arginine. In more particular embodiments the buffer comprises 5 to 25 mM phosphate and 0.15 to 0.75 M arginine. In still more particular embodiments the buffer comprises 10 to 20 mM phosphate and 0.3 to 0.5 M arginine. In other embodiments the buffer comprises 2.5 to 50 mM phosphate. In a related embodiment, the buffer comprises 5 to 25 mM Tris. In particular embodiments, the buffer comprises 10 to 20 mM Tris. In related embodiments the Tris buffer comprises histidine.

The liquid stable vaccines of the present invention can comprise an amino acid. In certain embodiments as detailed above, the amino acid is arginine. In other embodiments, the amino acid is methionine. In still other embodiments, the amino acid is glycine. In yet other embodiments, the amino acid is glutamic acid. In related embodiments, the liquid stable vaccines comprise both arginine and methionine. In other embodiments, the liquid stable vaccines comprise both arginine and glycine. In yet other embodiments, the liquid stable vaccines comprise both glycine and methionine. In related embodiments, the liquid stable vaccines comprise both glutamic acid and methionine. In other embodiments, the liquid stable vaccines comprise both glutamic acid and glycine. In yet other embodiments, the liquid stable vaccines comprise both glutamic acid and arginine.

In related embodiments, the liquid stable vaccines comprise arginine, glutamic acid, and methionine. In other embodiments, the liquid stable vaccines comprise arginine, glutamic acid, and glycine. In yet other embodiments, the liquid stable vaccines comprise arginine, glutamic acid, and methionine. In still other embodiments, the liquid stable vaccines comprise arginine, glycine, and methionine. In yet other embodiments, the liquid stable vaccines comprise arginine, glycine, and methionine. In particular embodiments, the liquid stable vaccines comprise arginine, glycine, methionine, and glutamic acid.

In particular embodiments the final concentration of arginine, or glutamic acid, or glycine in the liquid stable vaccine is 0.15 to 0.75 M. In related embodiments, the final concentration of arginine, or glutamic acid, or glycine in the liquid stable vaccine is 0.25 to 0.75 M. In more particular embodiments, the final concentration of arginine, or glutamic acid, or glycine in the liquid stable vaccine is 0.2 to 0.6 M. In more particular embodiments, the final concentration of arginine, or glutamic acid, or glycine in the liquid stable vaccine is 0.2 to 0.5 M. In still other embodiments, the final concentration of arginine, or glutamic acid, or glycine in the liquid stable vaccine is 0.25 to 0.45 M. In even more particular embodiments, the final concentration of arginine, or glutamic acid, or glycine in the liquid stable vaccine is about 0.45 M. In other particular embodiments, the final concentration of arginine, or glutamic acid, or glycine in the liquid stable vaccine is about 0.3 M.

In particular embodiments the final combined concentration of arginine together with glutamic acid and/or glycine in the liquid stable vaccine is 0.15 to 0.75 M. In related embodiments, the final concentration of arginine together with glutamic acid and/or glycine in the liquid stable vaccine is 0.25 to 0.75 M. In other embodiments, the final combined concentration of arginine together with glutamic acid and/or glycine in the liquid stable vaccine is 0.2 to 0.6 M. In more particular embodiments, the final combined concentration of arginine together with glutamic acid and/or glycine in the liquid stable vaccine is 0.3 to 0.5 M. In still other embodiments, the final concentration of arginine and glutamic acid, or glycine in the liquid stable vaccine is 0.25 to 0.45 M. In even more particular embodiments, the final combined concentration of arginine together with glutamic acid and/or glycine in the liquid stable vaccine is about 0.45 M. In other particular embodiments, the final concentration of arginine together with glutamic acid and/or glycine in the liquid stable vaccine is about 0.3 M.

In particular embodiments the final concentration of methionine in the liquid stable vaccine is 0.025 to 0.3 M. In related embodiments, the final concentration of methionine in the liquid stable vaccine is 0.04 to 0.15 M. In more particular embodiments, the final concentration of methionine in the liquid stable vaccine is 0.06 to 0.09 M. In even more particular embodiments, the final concentration of methionine in the liquid stable vaccine is about 0.07 M.

The liquid stable vaccines of the present invention also can comprise a stabilizer protein. The stabilizer protein can be an intact protein and/or a protein hydrolysate. In particular embodiments the stabilizer protein is gelatin. In more particular embodiments the stabilizer protein contained by the liquid stable vaccine of the present invention is 0.4 to 1.6% gelatin. In alternative embodiments the stabilizer protein is a hydrolysate of whole casein. In particular embodiments of this type the stabilizer protein contained by the liquid stable vaccine of the present invention is 0.5-2.0% of a hydrolysate of whole casein. In certain embodiments the hydrolysate of whole casein is a proteolytic hydrolysate of whole casein. In yet other embodiments, the stabilizer protein contained by the liquid stable vaccine of the present invention is lactoglobulin or a lactalbumin hydrolysate.

In addition, the liquid stable vaccines of the present invention can also further comprise a chelating agent. Such chelating agents can include, but are not limited to: ethylenediaminetetraacetic acid (EDTA), 1,2-bis(o-aminophenoxy)ethane-N,N,N',N'-tetraacetic acid (BAPTA), ethylene glycol tetraacetic acid (EGTA), dimercaptosuccinic acid (DMSA), diethylene triamine pentaacetic acid (DTPA), and 2,3-Dimercapto-1-propanesulfonic acid (DMPS). The concentration of such chelating agents in the liquid vaccines of the present invention can vary from about 50 μM to 10 mM.

In particular embodiments the chelating agent is ethylenediaminetetraacetic acid (EDTA). In certain embodiments of this type the liquid stable vaccine comprises 0.050 to 1 mM EDTA. In particular embodiments the liquid stable vaccine comprises 0.25 to 0.75 mM EDTA. In more particular embodiments the liquid stable vaccine comprises about 0.5 mM EDTA.

In certain embodiments the liquid stable vaccines of the present invention can further comprise one or more free radical scavengers and/or antioxidants as a component. In a particular embodiment of this type a vaccine of the present invention comprises ascorbic acid. In a particular embodiment of this type the liquid stable vaccine comprises about 0.5 mM ascorbic acid. In a related embodiment the vaccine comprises alpha-tocopherol. In a particular embodiment of this type the liquid stable vaccine comprises about 0.5 mM alpha-tocopherol. In yet another embodiment, the vaccine comprises glutathione. In a particular embodiment of this type the liquid stable vaccine comprises about 3 mM glutathione. In still another embodiment, the vaccine comprises both alpha-tocopherol and ascorbic acid. In yet another embodiment the vaccine comprises both alpha-tocopherol and glutathione. In still another embodiment, the vaccine comprises both glutathione and ascorbic acid. In yet another embodiment the vaccine comprises ascorbic acid, alpha-tocopherol, and glutathione.

In related embodiments, the liquid stable vaccines of the present invention are maintained in sealed containers. In particular embodiments of this type, the liquid stable vaccines of the present invention are maintained in sealed containers that have an inert gas such as argon, nitrogen, or helium, above the liquid (e.g., have been back-filled with the inert gas).

The liquid stable vaccines of the present invention can further comprise an adjuvant. In particular embodiments of this type, the adjuvant is aluminum phosphate. In other such embodiments, the adjuvant is aluminum hydroxide. In still other embodiments, the adjuvant is a low molecular weight copolymer adjuvant which can form cross-linkage in solution to become a high molecular weight gel. In yet other embodiments, the adjuvant is made up of gel particles of sodium acrylate in water. In still other embodiments the adjuvant is a combination of two or more such adjuvants.

In particular embodiments the liquid stable vaccines of the present invention can further comprise a detergent and/or surfactant. In a certain embodiments of this type the surfactant is a polyoxyethylene-polyoxypropylene block copolymer. In a particular embodiment of this type the liquid stable vaccine comprises about 0.01% polyoxyethylene-polyoxypropylene block copolymer. In a specific embodiment of this type the polyoxyethylene-polyoxypropylene block copolymer is PLURONIC® F-68.

The liquid stable vaccines of the present invention can comprise one or more live attenuated swine virus. In certain embodiments the live attenuated swine virus is transmissible gastroenteritis virus (TGE). In other embodiments the live attenuated swine virus is porcine reproductive and respiratory syndrome virus (PRRS). In yet embodiments the live attenuated swine virus is porcine epidemic diarrhea virus (PED). In still other embodiments the live attenuated swine virus is swine influenza virus (SIV). In yet other embodiments the live attenuated swine virus is porcine rotavirus (PRV). In still other embodiments the live attenuated swine virus is porcine parvo virus (PPV). In yet other embodiments, the live attenuated swine virus is porcine pseudorabies virus (PPRV). The present invention further provides any combination of two or more of these live attenuated swine viruses.

Accordingly, the present invention provides liquid stable vaccines that are multivalent vaccines. The multivalent vaccines of the present invention can contain any combination of porcine viruses. In certain embodiments the multivalent vaccines of the present invention comprise both killed porcine viruses and live attenuated porcine viruses. In specific embodiments, the multivalent vaccine comprises a live porcine reproductive and respiratory syndrome virus (PRRS) together with a live attenuated porcine epidemic diarrhea virus (PED) and/or a killed porcine circovirus antigen (PCV) and/or a recombinant subunit of PCV. In particular embodiments, the multivalent vaccine comprises killed SIV, killed and/or subunit porcine circovirus (PCV), together with live attenuated transmissible gastroenteritis virus (TGE) and live attenuated porcine parvovirus (PPV). In related embodiments, the multivalent vaccine comprises killed porcine circovirus antigen (PCV) and/or recombinant subunit thereof, killed swine influenza virus of multiple serotypes, live and/or killed attenuated transmissible gastroenteritis virus (TGE), and live attenuated porcine rotavirus (PRV).

The liquid stable vaccines of the present invention can further comprise a killed virus and/or a killed bacterium (e.g., a bacterin) and/or a sub-fraction of a bacterin. Accordingly, any of the liquid stable vaccines of the present invention that comprise one or more live virus vaccines can further comprise a killed virus and/or killed bacterium and/or a sub-fraction of a bacterin. In certain such embodiments these vaccines can further comprise adjuvants e.g., as indicated herein. In particular embodiments, the multivalent vaccine comprises one or more *Clostridium perfringens* inactivated toxoid, pilus antigen extracted from *E. coli* bacteria e.g., from any of the following serotypes: K99, K88, 987P, or F41, together with live attenuated transmissible gastroenteritis virus (TGE) and live attenuated porcine parvovirus (PPV). In alternative embodiments the multivalent vaccine comprises a live porcine reproductive and respiratory syndrome virus (PRRS) and a killed *Mycoplasma hyopneumoniae* (M. hyo), and/or an inactivated *Lawsonia intracellularis* bacterin. In a related embodiment, the multivalent vaccine comprises a killed porcine circovirus antigen (PCV) and/or a recombinant subunit of PCV, a killed *Mycoplasma hyopneumoniae* (M. hyo), an inactivated *Lawsonia intracellularis* bacterin, together with a live porcine reproductive and respiratory syndrome virus (PRRS).

The present invention further provides methods of aiding in the protection of swine against a clinical disease that arises from a swine virus infection comprising administering a vaccine of the present invention to the animal. Accordingly, the present invention provides methods that comprise administering to a porcine any of the liquid stable vaccines of the present invention. In certain embodiments the administration is performed mucosally (by intranasal or oral route). In other embodiments the administration is performed parenterally. In still other embodiments the administration is performed intradermally. In yet other embodiments the administration is performed transdermally. In other specific embodiments, a vaccine of the present invention is administered to the pig intramuscularly. The present invention also includes the use of primary and/or booster vaccines.

In particular embodiments, the method comprises administering to the pig a liquid stable vaccine of the present invention that comprises one or more live virus, e.g., a live attenuated virus. In specific embodiments the liquid stable vaccine comprises live attenuated PRRS, live attenuated TGE, a live PRV, live attenuated PED and/or live attenuated PPRV. In other embodiments the liquid stable vaccine comprises live attenuated PRRS, two serotypes of PRV, live attenuated TGE, and live attenuated PPRV as an expression vector for other vaccine antigens.

In addition, prior to, together with, or subsequent to administering any of the liquid stable vaccines of the present invention one or more attenuated or killed bacterial antigens such as *P. multocida, Salmonella* ssp., an *E. coli* including pilus types K99, K88, 987P, P41, *A. Pleuropneumoniae, B. Bronchiseptica, L. Intracellularis, M. Hyopneumoniae, C. perfringens* toxoids from types A, C, and/or D can also be administered. Examples of swine vaccines (both monovalent and multivalent) that contain antigens and combinations of antigens that can be included in the liquid stable vaccines of the present invention can be found in Tables 1A-1C below.

Methods of making any and all of the liquid stable vaccines of the present invention are also provided. In certain embodiments the method comprises combining a therapeutically effective amount of a live attenuated virus with a e.g., 5-40% (w/v) or 15-40% (w/v) sugar additive, (e.g., a sugar alcohol or a combination of a sugar alcohol with a non-sugar alcohol), an amino acid, and a buffered solution at pH 6.0 to pH 8.0 to form a liquid stable vaccine. The amino acid can be arginine, glycine, glutamic acid, methionine, or combinations of arginine, glycine, glutamic acid and/or methionine. In particular embodiments the arginine and/or glycine and/or glutamic acid has a final concentration of 0.15 to 0.75 M in the liquid stable vaccine. In certain embodiments the vaccine further comprises methionine at a final concentration of 0.025 to 0.3 M in the liquid stable vaccine. In particular embodiments the therapeutically effective amount of a live attenuated virus is a therapeutically effective amount of a live attenuated swine virus. In specific embodiments of this type, the therapeutically effective amount of a live attenuated swine virus includes therapeutically effective amounts of live attenuated TGE virus, live attenuated PRRS virus, live attenuated PRV, live attenuated PED virus, live attenuated PPRV and a live attenuated SIV virus, or a live attenuated virus expressing SIV proteins.

These and other aspects of the present invention will be better appreciated by reference to the following the Detailed Description and Example.

DETAILED DESCRIPTION OF THE INVENTION

Because the liquid stable swine virus vaccines of the present invention comprise live viruses, e.g., live attenuated viruses, heretofore particular care would have been needed during the formulation of the vaccine to maintain the titer of the attenuated viruses at a level that is safely below that which can lead to a significant adverse event. Indeed, most live attenuated swine virus vaccines are lyophilized, and lyophilization can lead to substantial declines in the efficacy of the attenuated live virus vaccines both due to the lyophilization process itself, as well as over time during long-term storage.

The present invention has overcome this problem by providing liquid stable swine vaccines that remain efficacious, even during storage, without needing to increase the initial titer of the live attenuated viral antigen above a reliably safe level. As an additional benefit, the present invention provides a means for lowering the cost of manufacture of the vaccines provided by significantly reducing the amount of live attenuated swine viruses necessary to make such a safe and efficacious vaccine. In addition, the live attenuated swine virus vaccines of the present invention are more convenient to use than their lyophilized counterparts. Accordingly, the present invention provides safe and efficacious live attenuated swine virus vaccines that can be stored as liquids at refrigerated temperatures and still remain stable for 5 to 7 months, 6 to 9 months, 9-12 months, 12 to 18 months, 18 to 24 months and/or even longer. Unlike its lyophilized counterpart, the liquid stable vaccines of the present invention do not have to be used as soon as it is rehydrated, because they are always hydrated. Since swine vaccines often come in 100 dose vials, as the largest presentation, those with larger farms will use hundreds of glass vials and discard the hazardous waste leftover from these vaccines in the trash. With the liquid stable swine vaccine, larger farms can buy larger packages (e.g., made of plastic) of vaccine, which they can use over weeks or months, providing the vaccine is handled properly and not contaminated, and then burn the residual plastic container when the vaccine is used up, thus decontaminating the container. This opens a whole new exclusive market of convenience to larger farms.

Moreover surprisingly, the liquid stable live swine virus vaccines of the present invention can include swine viruses of any type. Thus, the liquid stable live virus vaccines of the present invention can include both enveloped and non-enveloped swine viruses. In addition, the liquid stable live virus vaccines of the present invention can include live attenuated swine viruses having single-stranded RNA genomes, single-stranded DNA genomes, or double-stranded DNA genomes.

The use of singular terms for convenience in the description is in no way intended to be so limiting. Thus, for example, reference to a "sugar additive" includes reference to one or more of such sugar additives, unless otherwise specified. The use of plural terms is also not intended to be limiting, unless otherwise specified. Similarly, a chemical compound that can be referred to as an acid or its corresponding base, unless otherwise specified, when denoted herein as either is intended to mean either form of the compound. Thus, the use of the term glutamic acid is meant to include glutamate and vice versa.

As used herein, a "vaccine" is a composition that is suitable for application to an animal (including, in certain embodiments, humans) which upon administration to the animal induces an immune response strong enough to minimally aid in the protection from a clinical disease arising from an infection with a wild-type micro-organism, i.e., strong enough for aiding in the prevention of the clinical disease, and/or preventing, ameliorating, or curing the clinical disease.

Unless expressly indicated otherwise, the use of the term vaccine includes multivalent vaccines.

As used herein, a "multivalent vaccine" is a vaccine that comprises two or more different antigens. In a particular embodiment of this type, the multivalent vaccine stimulates the immune system of the recipient against two or more different pathogens.

As used herein, a "liquid stable" vaccine is a vaccine maintained as a liquid (including a liquid multivalent vaccine) that remains efficacious for at least six months when stored at or below 7° C. (e.g., in a standard refrigerator, and/or at 0° C.-7° C.). In particular embodiments a liquid stable vaccine remains efficacious when stored at or below 7° C. for at least 6 months. In even more particular embodiments a liquid stable vaccine remains efficacious when stored at or below 7° C. for at least 9 months. In still more particular embodiments a liquid stable vaccine remains efficacious when stored at or below 7° C. for at least 1 year. In yet more particular embodiments a liquid stable vaccine remains efficacious when stored at or below 7° C. for at least 1.5 years. In still more particular embodiments a liquid stable vaccine remains efficacious when stored at or below 7° C. for at least 2.0 to 3 years.

The terms "pig" or "swine" or "porcine" are all used interchangeably and include all domesticated porcine species, unless otherwise indicated.

As used herein, the terms "protect", "protecting", "provide protection to", "providing protection to", and "aids in the protection" do not require complete protection from any indication of infection. For example, "aids in the protection" can mean that the protection is sufficient such that, after challenge, symptoms of the underlying infection are at least reduced, and/or that one or more of the underlying cellular, physiological, or biochemical causes or mechanisms causing the symptoms are reduced and/or eliminated. It is understood that "reduced," as used in this context, means relative to the state of the infection, including the molecular state of the infection, not just the physiological state of the infection.

The term "prophylactically-effective amount" refers to the amount of a composition that when administered to swine significantly reduces the likelihood and/or extent of an infection/infestation due to a given pathogen.

"Metaphylaxis" is the timely mass medication of an entire group of animals to eliminate or minimize an expected outbreak of disease, e.g. in one or more animals at high risk of infection/infestation.

The term "chemoprophylaxis" refers to the administration of a medication/treatment, e.g., one or more prophylactic compositions, for the purpose of preventing or reducing viral, bacterial, and/or parasitic infection/infestation; and/or preventing or reducing disease and/or symptoms related to that infection/infestation.

The term "prophylactic composition" refers to any agent used singularly or in combination with other agents that significantly reduces the likelihood and/or extent of an infection/infestation due to a given pathogen in swine. In one such embodiment the swine are at high risk of developing swine enteric disease following commingling, changes in weather, changes in nutrition, and/or other stressors that can initiate a symptom and/or a disease related to the presence of the viral, bacterial, or parasitic pathogens commonly associated with swine, targeted by the agent or combination of agents.

As used herein, the term "therapeutically effective amount" is an amount of a given antigen, e.g., a live attenuated swine virus, which is sufficient to provide protection to and/or aid in the protection from the pathogen that the antigen is being administered to protect against, when provided in a single administration and/or when intended, provided as an initial administration with one or more subsequent booster administration(s).

As used herein, an "efficacious" vaccine comprises a therapeutically effective amount of a given antigen. An "efficacious" vaccine retains sufficient titer for a given antigen to be compliant with the regulatory requirements for that antigen for the jurisdiction where the vaccine is administered, e.g., the administration of a vaccine in the United States is governed by the United States Department of Agriculture (USDA).

As used herein, the term "pharmaceutically acceptable" is used adjectivally to mean that the modified noun is appropriate for use in a pharmaceutical product. When it is used, for example, to describe an excipient in a pharmaceutical vaccine, it characterizes the excipient as being compatible with the other ingredients of the composition and not disadvantageously deleterious to the intended recipient.

The term "carrier" refers to a diluent, adjuvant, excipient, or vehicle with which the compound is administered. Pharmaceutical acceptable carriers can be sterile liquids, such as water and/or oils, including those of petroleum, animal, vegetable or synthetic origin, such as peanut oil, soybean oil, mineral oil, sesame oil and the like. Water or aqueous solution saline solutions and aqueous sugar, e.g., dextrose and/or glycerol, solutions can be employed as carriers, particularly for injectable solutions. In addition, the carrier can be and/or comprise a hydrocolloid and/or polymer solution e.g., to thicken the porcine vaccines that are to be sprayed on to the pigs.

As used herein, an “adjuvant” is a substance that is able to favor or amplify the cascade of immunological events, ultimately leading to a better immunological response, i.e., the integrated bodily response to an antigen. An adjuvant is in general not required for the immunological response to occur, but favors or amplifies this response.

As used herein, “systemic administration” is administration into the circulatory system of the body (comprising the cardiovascular and lymphatic system), thus affecting the body as a whole rather than a specific locus such as the gastro-intestinal tract (via e.g., oral administration) and the respiratory system (via e.g., intranasal administration). Systemic administration can be performed e.g., by administering into muscle tissue (intramuscular), into the dermis (intradermal, transdermal, or supradermal), underneath the skin (subcutaneous), underneath the mucosa (submucosal), in the veins (intravenous) etc.

“Parenteral administration” includes subcutaneous injections, submucosal injections, intravenous injections, intramuscular injections, intradermal injections, and infusion.

As used herein a “sugar additive” is a 5 to 12 carbon sugar (e.g., sucrose, maltose, trehalose, dextrose, lactose, glucose, fructose, galactose) or sugar alcohol/polyol (e.g., sorbitol, mannitol, arabitol, inositol, maltitol). Unless otherwise specifically stated to the contrary, the percent (%) of the sugar additive is provided as a weight (w) of the sugar additive to the volume (v) of the vaccine, (w/v) in the vaccine.

As used herein a “non-reducing sugar” is a sugar additive which in basic aqueous medium does not generate any compounds containing an aldehyde group. Examples of non-reducing sugars of the present invention include sucrose and trehalose.

As used herein, the terms “non-sugar alcohol” and “non-alcohol sugar” are used interchangeably. A sugar additive that is a “non-sugar alcohol” (or “non-alcohol sugar”) as used herein, can be any sugar additive that is not a sugar alcohol, e.g., a non-reducing sugar.

As used herein, unless otherwise specifically stated to the contrary, the percent (%) of a solid additive, e.g., sugar additive or gelatin, in a vaccine is based on a 1% solution being 1 g of solid/100 ml of vaccine volume (w/v).

As used herein, unless otherwise specifically stated to the contrary, the percent (%) of a liquid additive, e.g., ethanol, in a vaccine is based on a 1% solution being 1 ml of liquid additive/100 ml of vaccine volume (v/v).

As used herein, the term, “approximately,” is used interchangeably with the term “about” and generally signifies that a value is within twenty-five percent of the indicated value, unless otherwise indicated, i.e., a concentration of “about” 2 mM EDTA can be 1.5 mM to 2.5 mM EDTA.

As used herein, unless otherwise specifically stated to the contrary, the pH value provided is the pH value determined/measured at 25° C.

Because the liquid stable vaccines of the present invention ideally range in pH from pH 6.0 to pH 8.0, the liquid stable vaccines of the present invention can comprise a buffer. Buffers for use in the liquid stable vaccines of the present invention include but are not limited to: potassium phosphate, sodium phosphate, Tris, Tris-Histidine, BIS-Tris, BIS-Tris-Propane, sodium or potassium pyrophosphate, imidazole, PIPES, ACES, MOPS, MOPSO, BES, TES, tricine, glycylglycine, and HEPES. The buffers can be brought to the desired pH with the use of any suitable counter ion.

The hydrolysate of whole casein that can be used in the liquid stable vaccines of the present invention can be obtained by a number of procedures including e.g., as an acid hydrolysate or an enzymatic hydrolysate. Such hydrolysates contain in the form of mixed amino acids and peptides having all of the amino acids originally present in casein. One pancreatic hydrolysate of whole casein that can be used in the liquid stable vaccines of the present invention is sold as CASEIN HYDROLYSATE ENZYMATIC® by MP Biomedicals. Comparable products are sold under the name of NZ-AMINE®, NZ-AMINE® A, NZ-AMINE® AS, and NZ-AMINE® B, and Tryptone by Sigma-Aldrich.

Examples of hydrocolloids that can be comprised by the vaccines of the present invention include: gelatin, starch polymers, and gums, such as xanthum gum, carragenin, and gum Arabic (acacia gum).

Multivalent Vaccines: The present invention provides liquid stable multivalent vaccines. A liquid stable multivalent swine vaccine of the present invention can include two or more antigens including one or more of the following live attenuated swine viruses: PRRS, PEDV, PRV, TGEV, PPRV, SW, and/or a recombinant SIV encoding one or more heterologous antigens. As noted above, a liquid stable multivalent swine vaccine of the present invention can also include one or more of the following live attenuated viruses: PRRS, PEDV, PRV, TGEV, PPRV, SW, and/or a recombinant SIV encoding one or more heterologous antigens, along with one or more killed swine viruses.

In addition, a liquid stable vaccine of the present invention can be subsequently combined with one or more live attenuated or killed bacterial vaccine comprising an antigen such as *Pasteurella multocida, Salmonella* ssp., *Escherichia coli* of multiple pillus types, *Actinobacillus pleuropneumoniae, Bordetella bronchiseptica, Mycoplasma hyopneumoniae, Lawsonia intracellularis, Erysipelas* spp., *Clostridium perfringens* and *Clostridium difficile* prior to administration. Examples of monovalent and multivalent vaccines that can be used in the liquid stable vaccines of the present invention are provided in Tables 1A-1C below:

TABLE 1A

| Live Virus Vaccines | |
|---|---|
| Single | Combo |
| Porcine reproduction and respiratory syndrome virus (PRRS) | Porcine rotavirus/*E. coli*/ *C. perfringens* Type C |
| Porcine Rotavirus (PRV) multiple serotypes | TGE/PRV/*C. perfringens* type C/ *E. coli* multiple pilus types |
| Transmissible gastroenteritis virus (TGE) | |

TABLE 1B

| Live Bacteria | |
|---|---|
| Single | Combo |
| *Salmonella cholerasuis* | *M. haemolytica*/*P. multocida* |
| *Mannheimia haemolytica* | *Lawsonia*/PCV/*M. hyopneumoniae* |
| *Pasteurella multocida* | |
| *Lawsonia intracellularis* | |

TABLE 1C

Killed Vaccines

| Single | Combo |
| --- | --- |
| *Clostridium Perfringens* Type A toxoid | *Clostridium perfringens* Type C/D toxoids |
| *Clostridium perfringens* Type C toxoid | Porcine Parvovirus, Erysipelas, *Leptospira canicola, pomona, hardjo-icterhaemorrhagia, Grippotyphosa* |
| *Clostridium perfringens* Type D toxoid | Swine influenza virus (multiple serotypes) |
| *Mycoplasma hyopneumoniae* | *C. perfringens* type C toxoid/*E. coli* |
| Porcine Circovirus | *E. coli* (multiple pilus types) |
| Porcine Parvovirus | *E. coli* (multiple pilus types)/*C. perfringens* type C |
| Swine Influenza virus | *B. bronchiseptica*/*P. multocida* |
| *Escherichia coli* multiple pilus types including K99, K88, 987P, Type 1 | |
| *Lawsonia intracellularis* | |
| *Bordetella bronchiseptica* | |
| *Actinobacillus pleuropneumoniae* | |

Adjuvants: The vaccines of the present invention can either contain an adjuvant or alternatively not contain an adjuvant, often depending on the antigen(s) that the vaccine contains. In particular embodiments, the adjuvant comprises an aluminum salt. The use of aluminum salts in conjunction with live viral vaccines has been described. In particular embodiments the aluminum salt is chosen from the group consisting of aluminum phosphate, aluminum potassium phosphate, and aluminum hydroxide. One aluminum phosphate adjuvant is REHYDROPHOS® (General Chemical, Parsippany, N.J.). Examples of aluminum hydroxide adjuvants include: REHYDROGEL®, REHYDROGEL® HPA, or REHYDROGEL® LV (General Chemical, Parsippany, N.J.). Other well-known adjuvants include hydrocarbon oils, polymers, saponins and/or an adjuvant made up of gel particles of sodium acrylate in water, e.g., MONTANIDE™ PET GEL A™ (Seppic, Paris France). One low molecular weight copolymer adjuvant can form cross-linkage in solution to become a high molecular weight gel, e.g., POLYGEN™ (MVP Laboratories, Omaha) When added, the amount of adjuvant is usually between about 1% and 20% (v/v) in the vaccine. In particular embodiments the amount of adjuvant is between about 2% to 10% (v/v). In more particular embodiments the amount of adjuvant is between about 3% to 6% (v/v).

Vaccine Administration: The liquid stable virus vaccines of the present invention may be administered by any conventional means, for example, by systemic administration, including by parenteral administration such as, without limitation, subcutaneous or intramuscular administration. The liquid stable virus vaccines of the present invention also may be administered by mucosal administration, such as by intranasal, oral, and/or ocular administration. Alternatively, the vaccines may be administered via a skin patch, in a delayed release implant, scarification, or topical administration. It is contemplated that a liquid stable virus vaccine of the present invention also may be administered via the drinking water and/or food of the recipient swine.

The vaccines (including multivalent vaccines) of the present invention also may be administered as part of a combination therapy, i.e., a therapy that includes, in addition to the vaccine itself, administering one or more additional active agents, therapies, etc. In that instance, it should be recognized the amount of vaccine that constitutes a "therapeutically effective" amount may be more or less than the amount of vaccine that would constitute a "therapeutically effective" amount if the vaccine were to be administered alone. Other therapies may include those known in the art, such as, e.g., analgesics, fever-reducing medications, expectorants, anti-inflammation medications, antihistamines, and/or administration of fluids.

The immunogenicity level may be determined experimentally by vaccine dose titration and challenge study techniques generally known in the art. Such techniques typically include vaccinating a number of animal subjects with the vaccine at different dosages and then challenging the animal subjects with the virulent virus to determine the minimum protective dose.

Factors affecting the preferred dosage regimen may include, for example, the breed (e.g., of a swine), age, weight, diet, activity, lung size, and condition of the subject; the route of administration; the efficacy, safety, and duration-of-immunity profiles of the particular vaccine used; whether a delivery system is used; and whether the vaccine is administered as part of a drug and/or vaccine combination. Thus, the dosage actually employed can vary for specific animals, and, therefore, can deviate from the typical dosages set forth above. Determining such dosage adjustments is generally within the skill of those in the art of vaccine development using conventional means.

Similarly, the volume with which such a dose can be administered typically lies between 0.1 mL (intradermal applications) and 2.0 mL. A typical range for the administration volume is between 0.2 and 1.0 mL, and about 0.2 to 0.5 mL for intradermal administration.

It is contemplated that the vaccine may be administered to the vaccine recipient at a single time or alternatively, two or more times over days, weeks, months, or years. In some embodiments, the vaccine is administered at least two times. In certain such embodiments, for example, the vaccine is administered twice, with the second dose (e.g., a booster) being administered at least 2 weeks after the first dose. In particular embodiments, the vaccine is administered twice, with the second dose being administered no longer than 8 weeks after the first dose. In other embodiments, the second dose is administered from 1 week to 2 years after the first dose, from 1.5 weeks to 8 weeks after the first dose, or from 2 to 4 weeks after the first dose. In other embodiments, the second dose is administered about 3 weeks after the first dose.

In the above embodiments, the first and subsequent dosages may vary, such as in amount and/or form. Often, however, the dosages are the same in amount and form. When only a single dose is administered, the amount of vaccine in that dose alone generally comprises a therapeutically effective amount of the vaccine. When, however, more than one dose is administered, the amounts of vaccine in those doses together may constitute a therapeutically effective amount. In addition, a vaccine may be initially administered, and then a booster may be administered from 2 to 12 weeks later, as discussed above. However, subsequent administrations of the vaccine may be made on an annual (1-year) or bi-annual (2-year) basis, regardless as to whether a booster was administered or not.

The vaccines of the present invention can also contain an anti-bacterial such as an antibiotic. Examples of such antibiotics can include: 10-1000 µg/mL gentamicin, 0.5-5.0 µg/mL amphotericin B, 10-100 µg/mL tetracycline, 10-100 units/mL nystatin (mycostatin), 10-100 units/mL penicillin, 10-100 μg streptomycin, 10-100 μg polymyxin B, and 10-100 μg neomycin.

The present invention may be better understood by reference to the following non-limiting Example, which is provided as exemplary of the invention. The following Example is presented in order to more fully illustrate embodiments of the invention. It should in no way be construed, however, as limiting the broad scope of the invention.

EXAMPLE

Stability of Liquid Swine Virus Vaccines

Materials and Methods

Bulk antigen preparation: Frozen bulk PRRS virus antigen was obtained and kept at <−50° C. until the time to blend the vaccine. The PRRS bulk antigen has a titer around 9 logs $\log_{10}(EID_{50})$.

Materials: US Pharmacopeial (USP) or higher grade sucrose and sorbitol are purchased from Fisher Scientific. Molecular biology grade L-arginine monohydrochloride with purity higher than 98% are purchased from Sigma. NZ Amine (bloom 250) solutions are prepared from the best available commercial reagents. The following solutions have been prepared and sterilized by autoclaving or 0.2 um filtration: 80% (w/v) sucrose, 70% (w/v) sorbitol, 2.3 M L-arginine monohydrochloride (pH 7.2), 5% (w/v) methionine hydrochloride solution, 45% (w/v) polyvinylpyrrolidone K-60, 0.5 M ethylenediaminetetraacetic acid (EDTA), Pleuronic F-68, 3 M glutamic acid, monosodium salt, 1.0 M potassium phosphate buffer (pH 7.2), tryptose phosphate broth (TPB) solution and 250 mg/mL gentamicin. Stock Solutions are summarized in Table 2A.

Stabilizer solution and vaccine blend pH adjustment: The pH of the final vaccine blend can be critical to the stability of the virus in liquid. The pH is measured using a very sensitive pH probe and meter. The meter displays the pH to 3 significant figures to the right of the decimal. There is a separate temperature probe with meter and both must be in the solution and stable. This pH meter is capable of a 5 point calibration curve with 3 points being an absolute minimum. During the vaccine blend preparation, the pH of the stabilizer solution is adjusted to the target pH prior to adding the virus antigen, and the pH is measured again after mixing the stabilizer solutions and virus antigens.

Preparation of the stabilizer solutions: Once the initial pH adjustment has been made, all formulations were filter sterilized using a 0.2 μM filter (PES is preferred filter matrix simply due to improved filter capacity). Currently filtration is performed using vacuum. A secondary benefit of vacuum filtering is the additional de-gassing of the formulation. After the formulation has been filter sterilized, it is sparged with argon gas to increase the depletion of $O_2$ which will hopefully yield lower reactivity of the formulation over time. Once the sparging is complete an argon overlay is placed prior to storage and a tight a seal is made. After the formulation is prepared, the pH is confirmed/adjusted to pH 7.2 at the desired temperature (e.g., 4°, 15°, or 25° C.), i.e., for many experiments performed herein the desired temperature was 4° C. If the formulation and previous procedures have been performed correctly the pH should be close to target pH. With an overnight incubation the pH may drift slightly due to the completion of chemical reactions associated with the earlier pH adjustment and further de-gassing.

Thawing virus bulk antigen: The frozen antigens are slowly thawed at room temperature (15-30° C.) or at refrigerated temperature (2-8° C.). The thawed antigen should be kept at 2-8° C. for no more than 8 hours prior to usage.

Preparation of vaccine blend: To make a 100 mL of vaccine blend, the volume of each stock solution required to reach the final concentration for each component as listed in Table 2B was calculated and then added to a sterilized container first, and the stabilizers and excipients were mixed using a stiffing bar. After the stabilizer solutions and all excipients were thoroughly mixed, the virus antigens at the indicated volume were added into the container and thoroughly mixed. The generating of bubbles and foams were avoided during this mixing step. When the virus is added in a very short time frame (a few minutes) then the virus may be added with no further issues. When the virus is not immediately added, an argon overlay is put in place to displace residual $O_2$. Once the virus has been added a fresh argon overlay is put into place prior to mixing. The argon gas is added to the bottle using a low flow rate. After the vaccine blending is complete, the vaccine blend is kept at 2-8° C. until dispensing into small aliquots.

Filling the vaccines: The vaccine blend was dispensed into glass ampule vials at 1.8 mL per vial. Each vial is then back-filled and overlaid with argon gas. The ampule vials were flame sealed, labelled and then transferred into boxes, and stored in the incubator at the designated temperature.

Stability testing at elevated temperature and real-time conditions: Liquid PRRS vaccines in ampule vials were stored at 27° C. and 4° C. respectively in the corresponding incubators. At the designated time point, 2 or more vials from each formulation were retrieved and the titer of each antigen was measured by tissue cell culture based virus titration assay.

Analytical Methods

PRRSv titration assay: The infectivity of test samples containing PRRSv is determined by titration on susceptible tissue culture cells, preferably African Green Monkey kidney cell lines such as MARC145 or MA104. Three to four days prior to the assay, cells are seeded into suitable culture plates or dishes, such as 96-well tissue culture plates.

In the following, the assay is described for standard 96-well tissue culture plates: Actively growing cells are seeded at $5\times10^4$ cells/well in assay media (for instance Dulbecco's Minimum Essential Media, supplemented with 10 mM HEPES, 2 mM L-Glutamine, 60 μg/mL Gentamycin and 7% fetal bovine serum), and incubated at 37° C. under 5% $CO_2$ atmosphere in a humidified incubator until use in the assay. On the day of the assay, appropriate serial dilutions of the test samples are prepared in assay media in dilution tubes, for instance glass tubes, or polypropylene tubes. For example, 10-fold dilutions may be prepared by adding 0.2 mL of undiluted test sample to 1.8 mL of assay media, briefly mixing by means of a vortex mixer, transferring 0.2 mL of the mixture into a separate test tube containing 1.8 mL of assay media, and so on.

For each test sample, one 96-well plate is removed from incubation, and the media is removed by inverting the plate and aseptically 'dumping' the media into a suitable receptacle. The sample is tested by adding 0.1 mL of each dilution to each of 10 wells on the plate. Dilutions are added from the highest dilution to the lowest dilution to be tested. Incubation is then continued for an additional 7 days.

Following incubation, the plates may be read either by visually observing cytopathic effects (CPE) using a light microscope at 100-1000× magnification, or macroscopically after staining with Crystal Violet (CV). In the CV method, a stock solution is prepared by dissolving 5 g of CV powder per 100 mL of 95% ethanol, followed by the addition of an equal volume of formaldehyde (37% stock solution), and the addition of deionized or better quality water to a final volume of 1,000 mL per 100 mL of ethanol. Media are removed from the 96-well plates by 'dumping', and CV stock solution is carefully added at 0.15 mL/well without disturbing remaining monolayers. The plate is left at ambient temperature for 15 minutes, after which the CV solution is removed by 'dumping'. The wells are then carefully rinsed under gently running tap water. Finally, the water is removed by 'dumping'.

Each well is observed for the absence of intact monolayers and presence of characteristic CPE indicative of PRRSv infection for both the CPE method and CV method. Wells are scored as positive or negative for signs of PRRSv infection. Virus titers are calculated according to the method of Spearman and Kärber, and are expressed as $Log_{10}$ $TCID_{50}$/mL.

Results and Conclusions

Table 2B below, lists 10 liquid stable formulations for swine virus vaccines of the present invention. Formulation 11 is a tryptone, lactose formulation that was designed in view of the freeze-drying methodology that was employed heretofore to stabilize live swine virus vaccines. In accelerated testing performed at 27° C., the standard freeze drying formulation (Formulation 11) started to fail immediately, see Table 3 below. In the corresponding real time stability study at 2° C.-7° C., the titer of all of the formulations were comparable to formulation 2 (see, Table 2B below). The titer of all of the 10 variations of this formulation appear to remain relatively stable at 2° C.-7° C. for at least 6 months, the final time point measured. In direct contrast, the titer of formulation 11 is measurably decreasing at this 6 month time point, having lost close to 1.5 logs of in its titer, see, Table 4 below.

TABLE 2A

STOCK SOLUTIONS

| Component | Concentration | pH |
|---|---|---|
| Sucrose | 80% (w/v) | N/A |
| Sorbitol | 70% (w/v) | N/A |
| L-arginine hydrochloride | 2.3M | pH 7.2 |
| L-methionine hydrochloride | 5% (w/v) | pH 7.2 |
| Polyvinylpyrrolidone K-60 | 45% (w/v) | N/A |
| EDTA | 0.5M | pH 7.2 |
| Pleuronic F-68 | 100% | N/A |
| L-glutamic acid, monosodium salt | 3M | pH 7.2 |
| Potassium phosphate buffer | 1M | pH 7.2 |
| Gentamicin sulfate solution | 250 mg/mL | N/A |

N/A indicates that the pH was not adjusted.

TABLE 2B

FORMULATIONS

| | Sucr. (% w/v) | Sorb. (% w/v) | ARG (M) | MET (% w/v) | GLU (M) | EDTA (mM) | F-68 (µL/mL) | K-60 PVP (% w/v) |
|---|---|---|---|---|---|---|---|---|
| 1 | 10 | 15 | 0.3 | | | | | |
| 2 | | 15 | 0.3 | | | | | |
| 3 | | 15 | 0.3 | 1.0 | | 0.5 | 0.8 | |
| 4 | | 15 | 0.3 | | | | | 0.5 |
| 5 | 20 | | 0.3 | 1.0 | | 0.5 | 0.8 | |
| 6 | | 15 | 0.3 | | | 0.5 | 0.8 | |
| 7 | | 15 | 0.3 | | | 2.0 | | |
| 8 | | 15 | 0.3 | | | 0.25 | | |
| 9 | | 15 | 0.25 | | | | | |
| 10 | | 15 | 0.46 | | | | | |

All 10 formulations were made up in potassium phosphate buffer pH 7.3; sucrose (Sucr.), sorbitol (Sorb.), arginine (ARG), methionine (MET), glutamic acid (GLU), ethylenediaminetetraacetic acid (EDTA), nonionic surfactant Pluronic F-68 (F-68), polyvinylpyrrolidone K-60 (K-60 PVP) were included as indicated.

TABLE 3

STABILITY TESTS at 27° C.

| Formultn. | 0 Time | 2 weeks | 4 weeks | 6 weeks |
|---|---|---|---|---|
| 1 | 6.2 | 4.4 | 3.6 | 0.7 |
| 2 | 5.6 | 4.6 | 3.6 | 1.0 |
| 3 | 6.3 | 4.8 | 3.5 | 0.7 |
| 4 | 6.0 | 5.0 | 3.4 | 1.0 |
| 5 | 6.3 | 4.9 | 2.8 | 0.6 |
| 6 | 5.9 | 5.1 | 3.6 | 1.3 |
| 7 | 5.8 | 4.7 | 3.6 | 1.1 |
| 8 | 5.9 | 3.9 | 0.5 | 0.5 |
| 9 | 6.1 | 5.0 | 3.1 | 0.7 |
| 10 | 5.8 | 4.5 | 0.6 | 0.6 |
| 11 | 6.2 | 1.4 | 0.5 | 0.5 |
| Control | 6.5 | 6.7 | 6.7 | 6.6 |

The values provided are the Log TCID50 virus. The times represent the storage times at 27° C. All of the formulations (Formultn.) are described in Table 2B above, except a commercial formulation (Formulation 11). The control is a sample of Formulation 11 that is maintained frozen prior to the assay. Formulation 11 comprised: 3.75% (w/v) Bacto Tryptone; 1.5% (w/v) dextran; 0.1% (w/v) gelatin; 5.0% (w/v) lactose; 0.1% (w/v) sodium glutamate; 0.5% (w/v) albumin Fraction V, and buffered with monobasic and dibasic potassium phosphate.

TABLE 4

STABILITY TESTS at 2°-7° C.

| Formultn. | 0 Time | 1 month | 2 months | 3 months | 6 months |
|---|---|---|---|---|---|
| 1 | 6.2 | 6.5 | 5.8 | 6.13 | 5.55 |
| 2 | 5.6 | 6.5 | 6.1 | 6.25 | 5.95 |
| 3 | 6.3 | 6.5 | 6.3 | 6.38 | 5.9 |
| 4 | 6.0 | 6.3 | 6.2 | 6.25 | 5.9 |
| 5 | 6.3 | 6.8 | 6.3 | 6.53 | 6.2 |
| 6 | 5.9 | 6.5 | 6.4 | 6.40 | 5.8 |
| 7 | 5.8 | 6.4 | 6.2 | 6.28 | 5.9 |
| 8 | 5.9 | 5.7 | 5.3 | 5.48 | 5.15 |
| 9 | 6.1 | 6.3 | 6.0 | 6.13 | 5.65 |
| 10 | 5.8 | 6.0 | 5.9 | 5.93 | 5.7 |
| 11 | 6.2 | 6.3 | 5.6 | 5.95 | 4.75 |
| Control | 6.5 | 6.7 | 6.7 | 6.7 | 6.7 |

The values provided are the Log TCID50 virus. The times represent the storage times at 2° C.-7° C. The control is a sample of Formulation 11 that is maintained frozen prior to the assay. The formulations (Formultn.) are described in Table 2B above, except the commercial formulation (Formulation 11) which is described in Table 3 above.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

We claim:

1. A liquid stable vaccine that comprises a live swine virus, a 5-40% (w/v) sugar alcohol, and 0.15 to 0.75 M of an amino acid selected from the group consisting of arginine, glutamic acid, and glycine; wherein the liquid stable vaccine has a pH of 6.0 to 8.0; and wherein the live swine virus is a Porcine Reproductive and Respiratory Syndrome Virus (PRRSV).

2. The liquid stable vaccine of claim 1 wherein the sugar alcohol is sorbitol.

3. The liquid stable vaccine of claim 2 wherein the amino acid is arginine.

4. The liquid stable vaccine of claim 3 that further comprises a live attenuated PED virus.

5. The liquid stable vaccine of claim 4 that further comprises a live attenuated Porcine Parvo Virus (PPV).

6. The liquid stable vaccine of claim 5 that further comprises a live attenuated Swine Influenza Virus (SIV) or a recombinant attenuated SIV vector that encodes a heterologous antigen.

7. The liquid stable vaccine of claim 6 that further comprises a live Porcine Pseudorabies Virus (PPRV), or a recombinant PPRV vector that encodes a heterologous antigen.

8. The liquid stable vaccine of claim 6 that further comprises a live attenuated Transmissible Gastroenteritis Virus (TGE virus).

9. The liquid stable vaccine of claim 3 that further comprises a bacterium selected from the group consisting of a live attenuated *Pasteurella multocida*, a live attenuated *Salmonella* ssp., a live attenuated *Mannheimia haemolytica*, a live attenuated *Lawsonia intracellularis*, a live attenuated *Clostridium perfringens*, a killed *Pasteurella multocida*, a killed *Salmonella* ssp., a killed *Actinobacillus pleuropneumonias*, a killed *Lawsonia intracellularis*, a killed *Mycoplasma hyopneumoniae*, a killed *Bordetella bronchiseptica*, a killed bacterin or extracted pilus antigen from any of the following types of *Escherichia coli*: K99, K88, 987P, or F41, an inactivated toxoid of *Clostridium perfringens*, and any combination thereof.

10. The liquid stable vaccine of claim 3, further comprising a live swine virus selected from the group consisting of a Transmissible Gastroenteritis Virus (TGE), Porcine Parvo Virus (PPV), Porcine Pseudorabies Virus (PPRV), Swine Influenza Virus (SIV), Porcine Epidemic Diarrheal Virus (PED), and any combination thereof.

11. The liquid stable vaccine of claim 10 that further comprises a killed swine virus.

12. The liquid stable vaccine of claim 1 further comprising a sugar additive that is a non-alcohol sugar, wherein the total amount of the sugar alcohol and the non-alcohol sugar in the liquid stable vaccine is 15-40% (w/v).

13. The liquid stable vaccine of claim 12 wherein the non-alcohol sugar is selected from the group consisting of sucrose and trehalose.

14. The liquid stable vaccine of claim 1 that further comprises a buffer.

15. The liquid stable vaccine of claim 14 wherein the buffer comprises 2.5 to 50 mM potassium phosphate.

16. The liquid stable vaccine of claim 1, wherein the amino acid is arginine.

17. A method of vaccinating a pig against PRRSV comprising administering to the pig the liquid stable vaccine of claim 1.

18. The method of claim 17, wherein said administering is performed by a method selected from the group consisting of intranasal spray, intramuscular injection, intradermal injection, subcutaneous injection, and feeding.

19. A liquid stable vaccine that comprises a live Porcine Reproductive and Respiratory Syndrome Virus (PRRSV), at least 10 to 20% (w/v) sugar alcohol, and 0.25 to 0.45 M arginine; wherein the liquid stable vaccine has a pH of 6.0 to 8.0.

20. The liquid stable vaccine of claim 19, wherein the sugar alcohol is sorbitol.

21. The liquid stable vaccine of claim 20, that further comprises 5-20% (w/v) sucrose.

22. The liquid stable vaccine of claim 20, that comprises 15% (w/v) sorbitol, and 0.3 M arginine.

23. A method of making a liquid stable vaccine that comprises combining a therapeutically effective amount of a live attenuated Porcine Reproductive and Respiratory Syndrome Virus (PRRSV) with a 5-40% (w/v) sugar alcohol, and 0.15 to 0.75 M arginine; wherein the liquid stable vaccine has a pH of 6.0 to 8.0.

* * * * *